United States Patent [19]
Hack et al.

[11] Patent Number: 5,906,809
[45] Date of Patent: *May 25, 1999

[54] ONE-STEP METHOD AND PREPARATION FOR REDUCING DENTINAL HYPERSENSITIVITY

[75] Inventors: Gary David Hack, Columbia; Van Purdy Thompson, Riva; Joseph Anthony von Fraunhofer, Baltimore, all of Md.

[73] Assignee: University of Maryland, Baltimore, Baltimore, Md.

[ * ] Notice: This patent issued on a continued prosecution application filed under 37 CFR 1.53(d), and is subject to the twenty year patent term provisions of 35 U.S.C. 154(a)(2).

[21] Appl. No.: 08/545,124

[22] Filed: Oct. 19, 1995

[51] Int. Cl.$^6$ .............................. A61K 6/02; A61K 7/16; A61K 6/08
[52] U.S. Cl. ..................... 424/49; 106/35; 433/228.1; 433/224; 433/217
[58] Field of Search ................ 424/49.58; 106/35; 433/228.1

[56] References Cited

U.S. PATENT DOCUMENTS

| | | | |
|---|---|---|---|
| 3,122,483 | 2/1964 | Rosenthal | 167/93 |
| 3,699,221 | 10/1972 | Schole et al. | 424/49 |
| 3,863,006 | 1/1975 | Hodosh | 424/49 |
| 3,988,434 | 10/1976 | Schole et al. | 424/49 |
| 4,057,621 | 11/1977 | Pashley et al. | 424/49 |
| 4,343,608 | 8/1982 | Hodosh | 433/224 |
| 4,538,990 | 9/1985 | Pashley | 106/35 |
| 4,588,756 | 5/1986 | Bowen | 106/35 |
| 4,659,751 | 4/1987 | Bowen | 106/35 |
| 4,675,120 | 6/1987 | Martucci | 252/8.553 |
| 4,952,613 | 8/1990 | Hosoda | 106/35 |
| 5,234,971 | 8/1993 | Imai et al. | 523/113 |

OTHER PUBLICATIONS

Suge et al C.A. 124:135663 of J. Dent. Res. 74(10):1709–1714(1995).
Nakajima C.A. 121:141755 of JPN 06116153 (Apr. 26, 1994).
Pereira C.A. 119:167518 of Braz. Pedido BR 9104700 (May 4,1993).
Imai et al (II) C.A. 115:214889, UK 6T.BR. 2239601 (Jul. 10, 1991).
Pashley et al (II) C.A. 102:31929 of J. Periodontol 55(9):522–523 (1984).
Pashley et al (II) C.A. 88:55104 of U.S. 4057621 (Nov. 8, 1977).
Mongiorgi et al CA 118:87364 of Bull. Soc. Ital. Biol. Sper. 68(2) 99–103 1992.
Schole et al (I) C.A. 78:33928 of U.S. 3699221 (Oct. 17, 1972).
Haveman et al Am. J. Dent. 7(5):247–251 Oct. (1994).
Cvenin et al J. Periodontol 62(11):668–673(Nov. 1991).
Kerns et al J. Periodontol. 62(7):421–428(Jul. 1991).
Collaert et al Endodontics & Dental Traumatol 7(4):145–152 Aug. 1991.
Hodosh et al Quintessence 6:495–502 Jun. 1991.
Mazor et al Clinical Prev. Dent. 13(3):21–25 May Jun. 1991.
Rosenthal (II) Dental Clinics of North America 34(3):403–427 Jul. 1990.
Muzzin et al J. Periodontol 60(3):151–158 Mar. 1989.
Knight et al., "Hypersensitive Dentin: Testing of Procedures for Mechanical and Clinical Obliteration of Dentinal Tubuli", J. Periodontol 64:5, pp. 366–373 (May, 1993).

*Primary Examiner*—Shep K. Rose
*Attorney, Agent, or Firm*—Chalin A. Smith; Office of Research & Development

[57] ABSTRACT

A highly acidic oxalate ion-containing preparation, which includes a neuroactive substance, for reducing tooth hypersensitivity, and a method for using same are disclosed.

28 Claims, 1 Drawing Sheet

ONE-STEP METHOD AND PREPARATION FOR REDUCING DENTINAL HYPERSENSITIVITY

FIELD OF THE INVENTION

The instant invention relates to a dental preparation for reducing tooth hypersensitivity and a method for using same to reduce tooth hypersensitivity.

BACKGROUND OF THE INVENTION

Tooth hypersensitivity is a common problem which affects about 40 million adults in the United States, 10 million of which can be considered chronically affected (Kanapka, Dent. Clin. North Am., 34:54, 1990). It is estimated that some 17% of adults in the U.S. have at least one or more sensitive teeth. The teeth may be sensitive to cold, heat, air or sweet foods.

The incidence of tooth hypersensitivity increases with age. The increased incidence is believed to be related to the general increase in exposed root surfaces of the teeth resulting from periodontal disease, tooth brush abrasion or cyclic loading fatigue of the thin enamel near the dento-enamel junction.

One theory to explain tooth hypersensitivity is based on the belief that open dentinal tubules allow fluid flow through the tubules. The flow excites the nerve endings in the dental pulp. Clinical replicas of sensitive teeth viewed in the scanning electron microscope (SEM) reveal varying numbers of open or partially occluded dentinal tubules.

Tubules generally are not seen at the tooth root surface because the cementum covering the tooth root or a smear layer of dentinal debris 2–5 $\mu$m in thickness that covers the tooth surface masks the tubules. When the smear layer of the tooth is present, the fluid flow that can occur through the dentin is only a few percent of that possible following acid removal of the smear layer, which treatment "opens" the tubules.

There is a growing body of evidence that occlusion of the dentinal tubules of a sensitive tooth, whether by resin infiltration, varnish coat or more recently by crystallite precipitation, results in reduction or elimination of hypersensitivity. The duration of relief, however, is highly variable. Hypersensitivity usually reappears because of tooth brush abrasion, the presence of acid challenges in the mouth or degradation of the coating material.

A two-step procedure for reducing hypersensitivity, involving application of a calcium nitrate solution and a potassium phosphate solution to the tooth, was believed to produce calcium phosphate crystals which were believed to occlude tubules (Kaminske et al., J. Dent. Res., 69:68, 1990).

Increasing concentrations of oxalic acid in the food bolus by including foods high in oxalic acid in the diet, up to 1.14 g/l of oxalic acid resulting in a pH of about 2, yielded precipitation of a deposit at the tooth surface. A maximal response was found at a level of 0.1% (w/v) oxalic acid equivalents. However, greater levels of oxalic acid did not yield greater protection of the teeth. It was postulated that the deposited material was calcium oxalate resulting from interaction of the oxalic acid with calcium in the saliva (Gortner et al., J. Nutr., 32:121, 1946), although the level of calcium in saliva is very low.

Alkali metal or ammonium oxalate also has been used to reduce tooth hypersensitivity. The low pH of about 2 of the solution is believed to mobilize calcium and phosphate from the hard tissues (U.S. Pat. No. 4,057,621).

In addition, a 3.0% (w/v) monohydrogen monopotassium oxalate solution, usually having a pH of about 2, was found to occlude dentinal tubules (Pashley et al., Arch. Oral. Biol., 23:1127, 1978). However, on closer examination, that treatment regimen deposited very few crystals on the dentin surface or within the tubules, and the deposited crystals are removed readily by water irrigation (Knight et al., J. Periodontol., 64:366–373, 1993). Minimal crystal precipitation and poor adherence of the crystals to dentin were confirmed independently.

Desensitizing dentifrices containing potassium oxalate have been found to provide temporary tubule occlusion (Pashley et al., J. Periodontol., 55:522, 1984). Potassium oxalate is thought to react with the smear layer to increase the resistance thereof to acid attack, as well as to reduce fluid permeability. It was thought that calcium oxalate crystals were produced when the dentin was treated with potassium oxalate (Pashley et al., Arch. Oral Biol., 30:731, 1985).

A two-component kit comprising a first 1–30% (w/v) neutral oxalate solution, such as dipotassium oxalate, and a second subsequent 0.5–3% (w/v) acidic oxalate solution, such as monopotassium-monohydrogen oxalate with a pH of 2 or as low as 1, has been described. It is alleged that the neutral oxalate forms large crystals over the dentinal surface and the acidic oxalate forms smaller crystals around and about the previously formed larger crystals, so as to form a combined layer of microscopic crystals (U.S. Pat. No. 4,538,990). However, examination of dentin surfaces subjected to treatment by the two-component kit described in U.S. Pat. No. 4,538,990 were found essentially to be free of deposited crystals and the tubules were non-occluded or open.

Studies on the occlusion of dentinal tubules by deposition of crystals from potassium oxalate-based media (30% (w/v) $K_2C_2O_4$ and 3% (w/v) $KHC_2O_4$) showed variable results, purportedly due to variations in the size and number of crystals generated by the two solutions. The rate of crystal formation was alleged to be influenced by the local $Ca^{2+}$ ion concentration, and it was stated that the acidic 3% (w/v) solution of $KHC_2O_4$ with a pH of about 2 generates an extremely high local calcium ion concentration by etching the tooth, allegedly resulting in accelerated formation of abundant crystals (Muzzin et al., J. Periodont., 60:151, 1989).

An effective two-step method of sealing dentinal tubules is the subject of copending application Ser. No. 08/282,960 filed Aug. 1, 1994. However, for reasons of clinical expediency, there is need for an effective and efficient one-step procedure for sealing dentin tubules.

A one-step method for occluding dentinal tubules, PROTECT™ (J. O. Butler, Chicago, Ill.), involves the application of a 3% (w/v) aqueous solution of $KHC_2O_4$ having a pH of about 2 to the tooth surface. The solution does not contain calcium salts because it is believed that etching of the tooth structure by the reagent contributes a more than adequate supply of $Ca^{2+}$ to enable sufficient precipitation and crystal formation, when the compound is applied to the tooth surface or in the tubule. However, it was observed that PROTECT™ has limited effectiveness because many tubules remain open.

A 6% (w/v) ferric oxalate in nitric acid solution having a pH of about 3 and a dentin bonding product known as TENURE™, which is a 3% (w/v) aluminum oxalate in nitric acid solution with a pH of about 1, were found to be insufficient in achieving adequate dentinal tubule occlusion and pain relief.

SUMMARY OF THE INVENTION

An object of the instant invention is to provide a preparation for reducing tooth hypersensitivity.

Another object of the instant invention is to provide a method for reducing tooth hypersensitivity.

Those and other objects of the instant invention, which will be apparent from a reading of the detailed description of the invention provided hereinafter, were met by a dental preparation comprising an oxalate ion and a neuroactive substance, wherein the pH of the preparation is less than 1.

In another embodiment, the above-described objects were met by a method for reducing tooth sensitivity comprising contacting a tooth surface with a dental preparation comprising an oxalate ion and a neuroactive substance, wherein said preparation has a pH of less than 1.

BRIEF DESCRIPTION OF THE DRAWINGS

FIG. 1A depicts a control sample which was untreated and was not exposed to the one-step dental preparation of the instant invention. Note the numerous open tubules. FIG. 1B depicts a tooth surface exposed to the one-step dental preparation of the instant invention. Note the uniform layer of crystals over the tooth surface.

DETAILED DESCRIPTION OF THE INVENTION

Figure 1A:
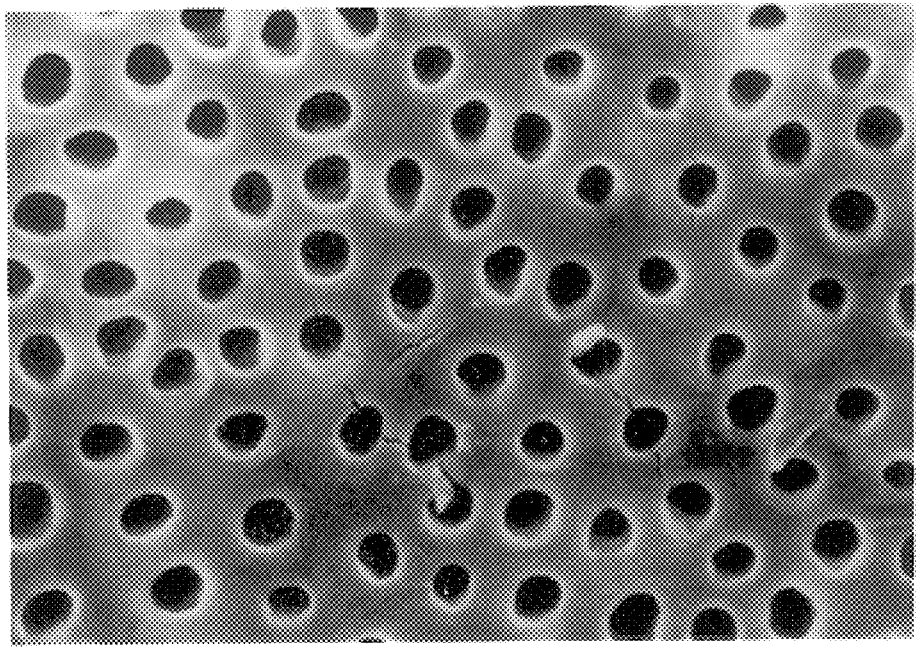
FIGS. 1A and 1B depict computer-generated reproductions of fields of tooth surfaces in the scanning electron microscope (SEM).

As discussed above, in one embodiment, the instant invention relates to a dental preparation comprising an oxalate ion and a neuroactive substance, wherein the pH of the preparation is less than 1.

The very high acidity required of the instant preparation results in an abundance of crystals at the tooth surface. The crystals are believed to occlude open dentinal tubules, which are thought to be a source of tooth hypersensitivity.

The instant preparation contains a neuroactive substance which serves as an analgesic. A suitable neuroactive substance is the strontium ion. If $Sr^{2+}$ ions are present in the preparation, $SrC_2O_4$ crystals also will precipitate and will be deposited at the tooth surface. The deposit both will occlude the dentinal tubules and will provide a source of the neuroactive $Sr^{2+}$ ions at the dentin surface and within the tubules through progressive, slow dissolution of the crystals.

Furthermore, when the preparation is made acidic with nitric acid, and the source of the oxalate ion is potassium oxalate, a by-product of the interaction of the preparation of the instant invention with dentin is $KNO_3$, a neuroactive salt specifically listed in the FDA register as a Class I material for the treatment of dentinal hypersensitivity.

As used herein, "oxalate ion", includes the monovalent $HC_2O_4^{-1}$ anion and the divalent $C_2O_4^{-2}$ anion.

As used herein, the term, "neuroactive substances", relates to any ion or salt which has a pain-reducing or analgesic activity. Examples include solutions of strontium salts, potassium citrate and potassium nitrate.

The low pH of the preparation of the instant invention is attained by using an inorganic acid in the instant preparation. The particular inorganic acid employed is not critical to the instant invention. Examples of such inorganic acids include nitric acid or hydrochloric acid. Nitric acid is preferred, particularly in a reaction comprising potassium, as the neuroactive salt, $KNO_3$, is produced.

The inorganic acid is used in an amount to obtain a pH of less than 1. Thus, generally, the instant preparation to contain about 1% to about 10% (v/v), preferably about 2% to about 5% (v/v), of inorganic acid. It is preferable to have a pH of less than about 0.9, less than about 0.8, less than about 0.7, less than about 0.6, and even less than about 0.5 to attain the abundant crystal formation that characterizes the instant invention.

The pH of less than 1 is essential, for example, to dissolve the smear layer preexisting at the tooth surface; to maintain the reactive reagents in the ionized state; to provide a local environment conducive to crystallization of the precipitating oxalate salt at the tooth surface; and to provide for a calcium ion-rich environment.

The source of the oxalate ion is not critical to the instant invention. The oxalate ion may be obtained from an oxalate salt, such as a univalent alkali metal oxalate, for example, one which contains the monovalent anion, or as a tetraoxalate salt, such as, potassium tetraoxalate, $KHC_2O_4 \cdot H_2C_2O_4$. The oxalate salts which can be employed in the instant invention may contain monovalent, divalent or trivalent cations, such as potassium, strontium, sodium, aluminum or ammonium cations. Potassium and strontium are desirable because both are neurally active with analgesic activity. Specific examples of such oxalate salts include monopotassium oxalate and dipotassium oxalate. The oxalate ion can be provided, for example, by dissolving oxalic acid or an oxalate salt in a liquid, such as, water.

Essentially saturating concentrations of the oxalate ion solutions can be prepared. In the case of monopotassium oxalate, about 17 g can be dissolved in hot water. That amount corresponds to about a 7% (w/v) solution.

Additionally, the preparation optionally may contain, as discussed above, a strontium salt to contribute a neuroactive, analgesic strontium ion. If the solution contains a suitable source of oxalate ion, the particular strontium salt employed is not critical to the instant invention. Examples of strontium salts include strontium nitrate, strontium oxalate and strontium chloride.

As discussed above, the preparation also and optionally can contain a potassium salt to yield a potassium ion that can contribute to the formation of neuroactive agents, such as potassium nitrate. The particular potassium salt employed is not critical to the instant invention. Examples of potassium salts include the potassium oxalates.

When a neurally active compound (or a compound which yields a neurally active ion) is included in the preparation, such as when strontium nitrate or strontium oxalate is included in the preparation, the neurally active compound is included in an amount of about 1% to about 8% (w/v). Strontium nitrate is highly soluble in aqueous media. A preferred range of strontium nitrate which is useful in the instant invention is from about 0.5% to about 2% (w/v).

In the case when strontium oxalate is used, and with other oxalates as well, the combined oxalate concentration should be not less than about 3% (w/v) and not exceed about 8% (w/v). A suitable concentration range of total oxalate ion is from about 3% to about 7% (w/v).

Suitable preparations of the instant invention include, for example, about a 7% (w/v) amount of oxalic acid in about a 2.5% (v/v) nitric acid solution and containing a strontium salt; about a 7% (w/v) amount of potassium tetraoxalate in about a 2.5% (v/v) nitric acid solution; and about a 7% (w/v) amount of potassium monohydrogen oxalate in about a 2.5% (v/v) nitric acid solution.

The form of the preparation of the instant invention is not critical thereto. For example, the preparation may be in the form an aqueous solution, a paste or a gel.

The preparation of the instant invention can contain various other non-essential additives to influence the state of the final product, such as, thickeners, preservatives, flavorants, fragrants and the like, as is well-known in the art, so long as the additives are compatible with and do not effect the low pH.

In another embodiment, the instant invention relates to a method for reducing tooth sensitivity comprising contacting a tooth surface with a dental preparation comprising an oxalate ion and a neuroactive substance, wherein said preparation has pH of less than 1. The composition of the preparation to be used in the instant method may be as provided hereinabove.

The tooth surface can be contacted with the preparation by applying the preparation using known applicators, such as a cotton pledget. As a gel or paste, the preparation may be applied by a brush or cotton pledget. The residence time of the reagent at the tooth surface should be at least about 2 minutes after which the reagent can be rinsed clean from the tooth.

The instant invention now will be exemplified by the following non-limiting example.

EXAMPLE

Figure 1B:
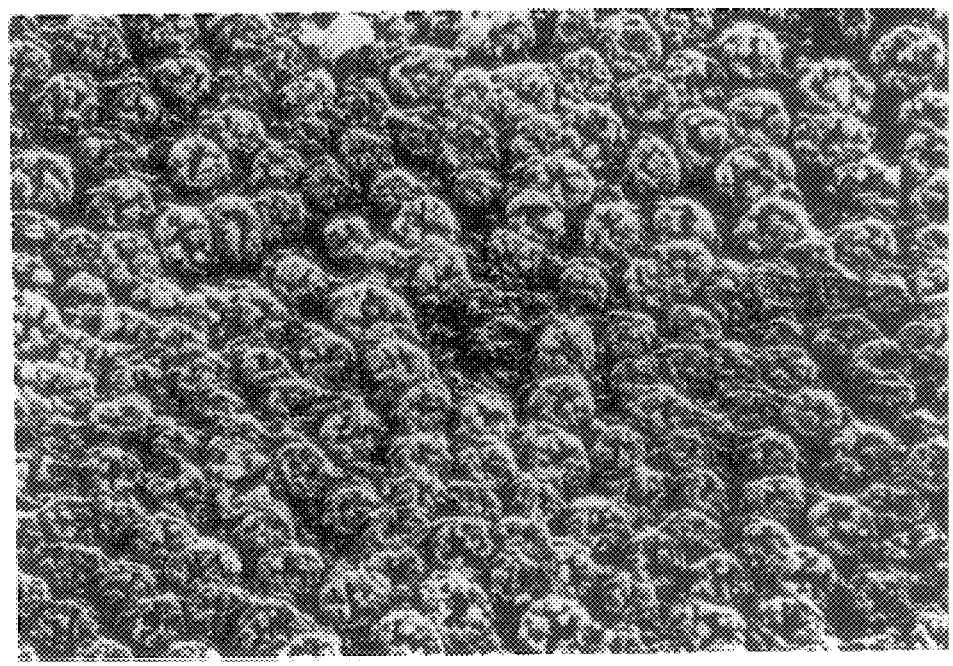

A dental preparation was prepared by dissolving about 6.8% (w/v) monopotassium oxalate in about a 2.5% (v/v) nitric acid solution to achieve a reagent having a pH of about 0.5. The resulting preparation, which yields the neuroactive potassium nitrate salt, was painted onto the tooth surface and an abundant precipitation of crystals which occlude dentinal tubules was observed by SEM. A parallel tooth surface that was not treated with the above preparation served as a control, see FIGS. 1A and 1B.

All references cited herein are incorporated herein by reference in entirety.

While the invention has been described in detail, and with reference to specific embodiments thereof, it will be apparent to one of ordinary skill in the art that various changes and modifications can be made therein without departing from the spirit and scope thereof.

What is claimed:

1. A dental preparation for reducing dentinal hypersensitivity due to the presence of exposed, open dentinal tubules consisting essentially of an oxalate ion and a neuroactive substance selected from the group consisting of potassium, calcium and strontium ions, wherein said preparation has a pH of less than 1, wherein said preparation both removes the smear layer from the surface of the exposed dentin of the tooth and creates a high concentration of calcium ions at said exposed dentinal surface and within the tubules of said exposed dentin so that dentinal tubule occluding calcium oxalate crystals are formed in situ, said crystals deposited upon said dentinal surface and within said dentinal tubules.

2. The preparation of claim 1, wherein said preparation has a pH of less than about 0.6.

3. The preparation of claim 1, wherein said preparation is in the form of an aqueous solution.

4. The preparation of claim 1, wherein said preparation contains nitric acid or hydrochloric acid.

5. The preparation of claim 1, wherein said preparation contains monopotassium oxalate or potassium tetraoxalate as a source of said oxalate ion.

6. The preparation of claim 1, wherein said neuroactive substance comprises a strontium salt.

7. The preparation of claim 6, wherein the strontium salt is selected from the group consisting of strontium nitrate, strontium chloride and strontium oxalate.

8. The preparation of claim 5, wherein said monopotassium oxalate or potassium tetraoxalate is present in an amount not less than about 3% (w/v).

9. The preparation of claim 8, wherein said monopotassium oxalate or potassium tetraoxalate is present in an amount of from about 3% (w/v) to about 7% (w/v).

10. The preparation of claim 7, wherein the strontium salt is strontium nitrate.

11. The preparation of claim 10, wherein said strontium nitrate is present in an amount of from about 0.5% (w/v) to about 2% (w/v).

12. The preparation of claim 7, wherein said strontium salt is strontium oxalate.

13. The preparation of claim 12, wherein said oxalate ion is present in a total amount of not less than about 3% (w/v).

14. The preparation of claim 13, wherein said oxalate ion is present in a total amount of from about 3% (w/v) to about 7% (w/v).

15. A method for reducing dentinal sensitivity due to the presence of exposed, open dentinal tubules consisting essentially of contacting an exposed dentinal surface with a dental preparation consisting essentially of an oxalate ion and a neuroactive substance selected from the group consisting of potassium, calcium and strontium ions, wherein said preparation has a pH of less than 1, wherein said preparation both removes the smear layer from the surface of the exposed dentin of the tooth and creates a high concentration of calcium ions at said exposed dentinal surface and within the tubules of said exposed dentin so that dentinal tubule occluding calcium oxalate crystals are formed in situ, said crystals deposited upon said dentinal surface and within said dentinal tubules.

16. The method of claim 15, wherein said preparation has a pH of less than about 0.6.

17. The method of claim 15, wherein said preparation is in the form of an aqueous solution.

18. The method of claim 15, wherein said preparation contains nitric acid or hydrochloric acid.

19. The method of claim 15, wherein said preparation contains monopotassium oxalate or potassium tetraoxalate as a source of said oxalate ion.

20. The method of claim 15, wherein said neuroactive substance comprises a strontium salt.

21. The method of claim 20, wherein the strontium salt is selected from the group consisting of strontium nitrate, strontium chloride and strontium oxalate.

22. The method of claim 19, wherein said monopotassium oxalate or potassium tetraoxalate is present in an amount not less than about 3% (w/v).

23. The method of claim 22, wherein said monopotassium oxalate or potassium tetraoxalate is present in an amount of from about 3% (w/v) to about 7% (w/v).

24. The method of claim 21, wherein the strontium salt is strontium nitrate.

25. The method of claim 24, wherein said strontium nitrate is present in an amount of from about 0.5% (w/v) to about 2% (w/v).

26. The method of claim 21, wherein said strontium salt is strontium oxalate.

27. The method of claim 26, wherein said oxalate ion is present in a total amount of not less than about 3% (w/v).

28. The method of claim 27, wherein said oxalate ion is present in a total amount of from about 3% (w/v) to about 7% (w/v).

* * * * *